| United States Patent [19] | | [11] | 4,030,994 |
|---|---|---|---|
| Kollonitsch | | [45] | June 21, 1977 |

[54] SUBSTITUTIVE FLUORINATION OF ORGANIC COMPOUNDS

[75] Inventor: Janos Kollonitsch, Westfield, N.J.

[73] Assignee: Merck & Co., Inc., Rahway, N.J.

[22] Filed: Oct. 9, 1973

[21] Appl. No.: 404,555

Related U.S. Application Data

[63] Continuation-in-part of Ser. No. 154,695, June 18, 1971, abandoned, which is a continuation-in-part of Ser. No. 60,645, Aug. 3, 1970, abandoned.

[52] U.S. Cl. .................. 204/159.11; 204/158 HA; 204/158 HE; 204/159.13; 204/159.14; 204/159.18; 204/159.19; 204/159.20; 204/163 R; 204/163 HE; 260/534 R; 260/534 C; 260/648 F; 260/649 F; 260/653; 260/653.1 R; 260/653.1 T; 260/653.4; 526/21; 526/22; 526/41; 526/46; 528/483; 528/487; 528/491; 528/494

[51] Int. Cl.² .................. C08F 2/46; C08F 2/54; C08F 8/00

[58] Field of Search .................. 204/159.13, 159.14, 204/159.18, 159.20, 159.11, 158 HA, 158 HE, 163 R, 163 HE, 159.19

[56] References Cited

UNITED STATES PATENTS

| 3,081,243 | 3/1963 | Feng | 204/159.18 |
|---|---|---|---|
| 3,104,214 | 9/1963 | D'Alelio | 204/159.18 |
| 3,151,051 | 9/1964 | Braid et al. | 204/159.18 |
| 3,456,024 | 7/1969 | Loree | 260/653 |

OTHER PUBLICATIONS

Cady, Proc. Chem. Soc., 133–138 (1960).
Allison et al., Abstract 63, A.C.S. Meeting, Chicago (1968).
Sheppard et al., *Organic Fluorine Chemistry* p. 231 (Benjamin, New York, N.Y. 1969).
Florocarbon and Related Chemistry, vol. I, (1971), Banks and Barlow p. 153.

*Primary Examiner*—Murray Tillman
*Assistant Examiner*—Thurman K. Page
*Attorney, Agent, or Firm*—Hesna J. Pfeiffer; Julian S. Levitt

[57] ABSTRACT

Organic compounds having at least one replaceable hydrogen atom are fluorinated in the liquid or solid state by treatment with fluoroxyperfluoroalkanes or fluoroxypentafluorosulfur under the influence of a free radical initiator.

8 Claims, No Drawings

SUBSTITUTIVE FLUORINATION OF ORGANIC COMPOUNDS

This application is a continuation-in-part of copending application Ser. No. 154,695, filed June 18, 1971, now abandoned, which in turn is a continuation-in-part of application Ser. No. 60,645, filed Aug. 3, 1970, now bandoned.

This invention relates to a novel process for the fluorination of organic compounds. In particular it relates to the fluorination of organic compounds in the liquid or solid phase with fluoroxyperfluoroalkanes or fluoroxypentafluorosulfur. Still more particularly it reltes to mono- or poly-fluorination of organic compounds with fluoroxyperfluoroalkanes or fluoroxypentafluorosuflur under conditions conducive to the formation of free radicals.

The novel process of this invention can be represented by the following equation:

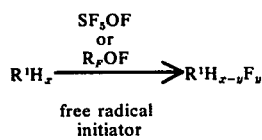

$R^1H_x$ represents an organic molecule having $x$ replaceable hydrogens linked to carbon. The numerical value of $x$ is at least 1 and can be as high as several thousand in the case of polymers. Where the substrate is a monomer $x$ is in the range of 1 to about 60. The subscript $y$ can be any number equal to or less than $x$. The organic molecule substrate can be virtually any such entity which is subject to free radical substitution and includes such as : (1) mono- and polynuclear carbocyclic aromatic compounds such as benzenes, naphthalenes, phenanthrenes, anthracenes, fluoroanthenes, pyrenes, chrysenes, indenes, fluorenes, naphthacenes, benzoquinones, naphthoquinones, phenanthrenquinones and the like; (2) mono- or poly-nuclear alicyclic compounds, such as the monocycloalkanes, poly- and perhydronaphthalenes, poly- and perhydrophenanthrenes, adamantane and the like; (3) alkanes and alkenes; (4) amino acids, either cyclic or acyclic, and either basic or acidic; (5) dihydrocarbyl dihalosilanes such as dimethyl dichlorosilane; (6) fatty acids and derivatives such as amides; (7) polymers such as polycaprolactam, polyethylene, polystyrene, polyisobutene, polyisoprene, polysiloxanes and the like; (8) heterocycles, such as pyridines, quinolines, isoquinolines, cinnolines, phthalazines, quinazolines, quinoxalines, acridines, phenanthridines, phenanthrolines, phenazines, pyridazines, imidazoles, pyrazoles, indoles, triazoles, indazoles, pyrroles, furans, thiophenes, piperidines, piperazines, pyrrolidines, azetidines, and the like. The organic substrates can be unsubstituted or substituted with any of the substituents commonly encountered such as halo, lower alkyl, lower alkoxy, amino, mono- or di(lower alkyl)amino, nitro, carboxyl, lower alkoxy carbonyl, sulfonyl, trihalomethyl, lower alkylthio, cyano, carboxamido, di(lower alkyl)carbamyl, lower akanoylamino sulfamoyl, mono- or di(lower alkyl)sulfamoyl, lower alkanoyl, and the like.

Of particular interest is the application of the novel fluorination process of this invention to polysiloxanes substituted with $C_{1-5}$ alkyl groups or phenyl groups such as dimethylpolysiloxane, methylpropylpolysiloxane, methylphenylpolysiloxane and diphenylpolysiloxane.

$R_FOF$ represents a fluoroxyperfluoroalkane wherein the alkyl group is of 1 to about 5 carbon atoms, such as fluoroxytrifluoromethane, fluoroxyperfluoroethane, 1- or 2-fluoroxyperfluoropropane, or 2-fluoroxyperfluoro-2-methylpropane, (bis)fluoroxydifluoromethane and 1,3(bis)fluoroxyperfluoropropane.

Prior to this invention the scope and utility of known methods for substitutive fluorination of organic compounds in the sense of the equation:

$$RH \rightarrow RF$$

were very limited. The most important methods available for the above type of transformation were (1) reaction with elementary fluorine, (2) electrolytic fluorination in liquid hydrogen fluoride, (3) reaction with high valency oxidative metallic fluorides such as cobalt trifluoride, (4) reaction with perchloryl fluoride, and (5) fluorination with fluoroxyperfluoroalkanes.

The main limitations with methods (1), (2) and (3) are that they usually result in mixtures of polyfluorinated compounds even in the case of substrates with simple structures. With more complex substrates, extensive degradation and carbon skeletal rearrangements often occur, this severely limiting the yield and predictability of any individual product. In contrast, method (4), employing perchloryl fluoride, allows more selective fluorination and does not generally cause degradation of the substrate, but is only effective with especially reactive substrates such as activated methylene groups.

Method (5), fluorination with fluoroxyperfluoroalkanes has been reported in the prior art. D. H. R. Barton et al., in Chemical Communications, 1968, 804, 806; 1969, 227 published on the fluorination of alkenes and aromatic compounds. The reactions described therein were electrophilic, proceeded in the "dark", i.e., in the absence of irradiation, and required "suitably activated" aromatic substrates. Allison et al. in J. Amer. Chem. Soc., 81, 1089–1091 (1959) also reported on "Reactions of Trifluoromethyl Hypofluorite with Organic Compounds". The reactions described were conducted at room temperature in the gas phase and were spontaneous of initiated with ultraviolet light or by a spark. In the case of alkenes, the fluoroxytrifluoromethane added across the double bond; benzene exploded to give a very low yield of fluorobenzene; and alkanes yielded the entire spectrum of fluorinated alkanes in low yield.

Surprisingly it has now been found that the limited usefulness of fluoroxyperfluoroalkanes and fluoroxypentafluorosulfur can be greatly extended by conducting the reaction in the liquid or solid phase under conditions conductive to the formation of free radicals.

The novel process of this invention comprises treating the substrate with a fluoroxyperfluoroalkane or fluoroxypentafluorosulfur under the influence of a free radical initiator such as light which includes ultraviolet light, ionizing radiations such as $\beta$-or $\gamma$-rays or microwaves, or chemical chain initiators such as azo compounds, for example, azo-bis-isobutyronitrile or combinations of such free radical initiators. One of the preferred modes of operation is to dissolve the substrate in a suitable solvent which is inert to the fluorination reaction such as fluorotrichloromethane or other similar halogenated alkane, or a strong acid such as liquid hydrogen fluoride, fluorosulfonic acid, trifluoroacetic acid or sulfuric acid; expose the solution to the free radical initiator; with vigorous stirring and maintenance of temperature, admit the required amount of the fluoroxy reagent slowly to the reaction mixture; and continue agitation and irradiation until reaction is complete.

Use of one of the strong acids as solvent is particularly advantageous in, but not limited to, those instances wherein the substrate carries one or more polar functional groups such as amino, alcohol, carboxyl, alkoxy or the like. In addition, if desired, a strong acid can be employed in combination with one of the non-acidic solvents.

Because of the low boiling point of the reagents it is convenient to conduct the reaction at temperatures as low as −80° C. in which case the reaction proceeds at atmospheric pressure. However if desired, the reaction can be executed at higher temperatures, for example, in the case of trifluoroacetic acid solvent, at −10° to +10° C.

A suitable reaction vessel for atmospheric pressure reactions is one machined from a Kel-F rod equipped with an ultraviolet-transparent window. Alternatively the reaction can be conducted in a pressure vessel such as a Hastelloy bomb or a steel bomb with a platinum lining, in which case higher temperatures, for instance up to about 100° C can be employed. In such case the use of $\alpha$-rays or x-rays as free radical initiator is convenient, as these high energy rays penetrate the wall of the reactor.

The above described process can be performed by conventional batch techniques, or alternatively it can be run in a continuous manner in a tubular reactor either with or without packing such as Raschig rings, saddles or the like through which the substrate or its solution and the fluorinating agent are pumped, preferably in a counter-current fashion while being exposed to radical generating radiation. This method of operation is particularly advantageous in cases where the particular substrate is subject to reaction with the fluoroxy compound even in the absence of radical generating conditions. In this case, by employing the above continuous technique it becomes possible to accelerate the radical type reaction, while leaving unchanged the rate of the non-radical reaction, thus raising the yield of the product formed by radical reaction.

A convenient source of radiation for radical greneration was found to be a Hanovia mercury-xenon arc lamp No. 9778-1, run by a 1000 W. power supply. The lamp was mounted in a Schoeffel LH 15 1-N Projector equipped with a quartz condensor lens and a heat filter (water).

The novel process of this invention provides a convenient route to a large variety of organic fluorine compounds. Such compounds are known to have wide ranging utility as, for example, solvents, intermediates in organic snythesis, insecticides, plant growth regulators, herbicides, refrigerants, lubricants, pharmaceuticals and so on.

5-Fluoro-2-methyl-1-(p-methylsulfinylbenzylidene)inden-3-acetic acid prepared by the novel process of this invention has utility as an antiinflammatory, analgesic and antipyretic agent. It can be administered orally, rectally, parenterally, or topically in doses of from 0.1 mg/Kg. to 50 mg/kg. per day.

4-(2-Phenyl-1,1,2,2-tetrafluoroethyl)-$\alpha,\alpha$-dimethylbenzylamine prepared by the novel process of this invention has utility as an antiarrhythmic agent. Administration of this compound or a pharmaceutically acceptable acid addition salt results in the prevention of arrhythmia in animals under conditions which ordinarily cause the development of arrhythmia and will arrest an existing arrhythmia in the animal being treated and cause a resumption of normal cardiac rhythm. As an antiarrhythmic agent it may be administered orally or parenterally. The formulations for administration may be prepared in conventional manner, employing conventional pharmaceutical carriers and excipients. The daily dose is based on the total body weight of the test animal and varies between about 1.00 and 100.00 mg./kg. for mature animals. Thus, a unit dose based on four-times-a-day administration is between 2.5 mg. and 250 mg. for a 10 kg. dog, and a total daily dose for a 10 kg. dog would vary between about 10 mg. and 1,000 mg. For larger animals, up to 100 kg. and above, proportional dosages are employed, based on the weight of the animal.

Fluorinated polycaprolactams, polyethylenes, polystyrenes, dimethyl polysiloxanes, and phenyl methyl polysiloxanes, all preparable by the process of this invention have the varied utilities usually associated with the plastic and synthetic fiber industries but have the added feature of increased resistance to chemical attack, particularly by oxidative agents.

Similar utility is found for the monomeric di(mono-, di-, and trifluoromethyl)dichlorosilanes which can be prepared by this novel process. They are readily converted to fluorinated dimethyl polysiloxanes by techniques well known to polysiloxane technology.

The novel process of this invention is the only method suitable for fluorination of organosilicones, either monomer or polymer, as the art recognized fluorination techniques invariably cause scission of the C-Si bond and formation of the Si-F bond.

In addition the novel process provides a useful route to many new compounds and new compositions of matter such as 3-fluoro-D-alanine, a compound displaying antibacterial activity against several classes of pathogenic micro-organisms, 3-fluoro-L-azetidine-2-carboxylic acid, 3-, and 4-fluoro-1-aminoadamantane, difluoro-$\epsilon$-aminocaprolactam, and trifluoro-$\epsilon$-aminocaprolactam.

3-Fluoro-D-alanine is also obtained by resolution of the known 3-fluoro-D,L-alanine by any known resolution means. One such method is to form the carbobenzyloxy derivative of the D,L-mixture followed by preparation of the salt with d- or 1-$\alpha$-phenethylamine. The salt with 1-$\alpha$-phenethylamine provides the carbobenzyloxy derivative of 3-fluoro-D-alanine. Hydrogenolysis of the carbobenzyloxy group yields the desired 3-fluoro-D-alanine.

EXAMPLE 1

Fluorination of benzene with fluoroxytrifluoromethane

With the reactor immersed in a dry-ice-acetone bath, and with vigorous stirring and irradiation with ultraviolet light, 2.7 g. of fluoroxytrifluoromethane gas was introduced over a period of 1 hour to a solution of 2.03 g. of benzene in 80 ml. of fluorotrichloromethane. After an additional hour of irradiation under similar conditions, the mixture was subjected to separation by preparative gas-liquid chromatography on a column filled with 20% QF-1 (Dow Corning brand of methylsilicone) on Gas-chrom Z (silylated diatomaceous earth) at 90° C. The yield of fluorobenzene was 0.87 g. (65% of theory, based on recovery of 0.93 g. of benzene).

EXAMPLE 2

Fluorination of benzene with fluoroxypentafluorosulfur

Benzene (0.78 g., 0.01 mole), dissolved in 55 ml. of fluorotrichloromethane was ultraviolet irradiated and 3.24 g. fluoroxypentafluorosulfur (0.02 mole) was passed into it in a period of 20 min., while being stirred in a dry-ice-acetone bath. After 1 hour further ultraviolet irradiation, the solvent was distilled off and the residue analyzed by glc-mass spectrometry, to indicate the formation of fluorobenzene as the principal reaction product.

Employing the procedure of Example 1 or 2, but substituting for the benzene employed therein an equivalent amount of the aromatic starting materials shown in Table I, there is produced the fluoro-aromatic products, also shown in Table I.

TABLE I

| Example | Starting Material | Product |
| --- | --- | --- |
| 3 | naphthalene | 1-fluoronaphthalene<br>2-fluoronaphthalene |
| 4 | anthracene | mixture of fluoro-anthracenes |
| 5 | indene | 2-fluoroindene<br>3-fluoroindene |
| 6 | phenanthrene | mixture of fluoro-phenanthrenes |
| 7 | fluorene | mixture of fluoro-fluorenes |
| 8 | N-acetyl-α-naphthylamine (1) | fluoro-N-acetyl-α-naphthylamine |
| 9 | chlorobenzene | fluoro-chlorobenzene |
| 10 | α-chloronaphthalene | fluoro-chloronaphthalene |
| 11 | 1-amino-2-chloro-naphthalene (1) | fluoro-1-amino-2-chloro-naphthalene |

(1) solvent is hydrofluoric acid or trifluoroacetic acid

EXAMPLE 12

Fluorination of 4,4'-bis-acetamino-diphenylsulfone 4,4'-Bis-acetamino-diphenylsulfone (3.4 g.) was dissolved in 32 ml. of trifluoroacetic acid, cooled to −12° C. then under stirring and ultraviolet irradiation 2.1 g. of fluoroxytrifluoromethane was introduced over about one hour and irradiation was continued for another two hours. Another 1 g. quantity of fluoroxytrifluoromethane was added over about one hour, followed by an irradiation period of 2½ hours. The temperature was kept at −10°–0° C.

The residue obtained after evaporation of trifluoroacetic acid in vacuo was treated with water and sodium bicarbonate solution, washed with water and dried in vacuo to give a light-tan crystalline product, which according to glc-mass spectrometry, represented a 1:1 mixture of 3-fluoro and 3,3'-difluoro-4,4'-bis-acetamido-diphenylsulfone.

Similarly, 4-nitro-4'-acetamido-diphenylsulfone was photofluorinated in trifluoroacetic acid to give 3'-fluoro-4-nitro-4'-acetamido-diphenylsulfone, m.p. 232°–33° C., after recrystallization from methanol.

EXAMPLE 13

Fluorination of Anisole

Anisole (1.62 g., 0.015 mole), dissolved in 50 ml. of fluorotrichloromethane was stirred and irradiated with ultraviolet light at about −80° C., while 1.14 g. (0.011 mole) of fluoroxytrifluoromethane gas was passed in over ½ hour. The irradiation and stirring were continued for another ½ hour. The solvent was evaporated, and the residual clear oil was analyzed by gas-liquid chromatography and mass spectrometry. The product consisted of 58% of anisole, 38% of o-fluoroanisole and 4% of a mixture of m- and p-fluoroanisole. (Gas-liquid chromatography was on 10 feet × ¼ inch 20% QF-1 on 80/100 mesh Gas-Chrom Z; column 150° C., detector 260° C., injection 175° C.).

EXAMPLE 14

Fluorination of Toluene

Into a solution of toluene (1.38 g., 0.015 mole), dissolved in 50 ml. of fluorotrichloromethane, 1.9 g. of fluoroxytrifluoromethane (0.019 mole) was passed in during a ½ hour period while being stirred and ultraviolet irradiated under cooling in a dry-ice-acetone bath. The ultraviolet irradiation and stirring were continued for another 40 min. Gas-liquid chromatographic analysis, combined with mass spectrometry, indicated that o-fluorotoluene and benzylfluoride were the main reaction products.

EXAMPLE 15

5-Fluoro-2-methyl-1-(p-methylsulfinylbenzylidene)inden-3-acetic acid

Step A: 2-Methylinden-3-acetic acid

2-Methylindanone (0.112 mole), cyanacetic acid (10.5 g., 0.123 mole), acetic acid (6.6 g.), and ammonium acetate (1.7 g.) in dry toluene (15.5 ml.) was refluxed with stirring for 21 hrs., as the liberated water was collected in a Dean Stark trap. The toluene was concentrated and the residue dissolved in 60 ml. of hot ethanol and 14 ml. of 2.2 N aqueous potassium hydroxide solution. 22 g. Of 85% KOH in 150 ml. of water was added and the mixture refluxed for 13 hr. under $N_2$. The ethanol was removed under vacuum, 500 ml. water added, the aqueous solution washed well with ether and then boiled with charcoal. The aqueous filtrate was acidified to pH 2 with 50% hydrochloric acid, cooled and the precipitate of 2-methylinden-3-acetic acid was collected.

Step B:

2-Methyl-1-(p-methylthiobenzylidene)inden-3-acetic acid

2-Methylinden-3-acetic acid (0.072 mole) p-methylthiobenzaldehyde (14.0 g., 0.091 mole) and sodium methoxide (13.0 g., 0.24 mole) were heated in methanol (200 ml.) at 60° C. under nitrogen with stirring for 6 hr. After cooling, the reaction mixture was poured into 750 ml. of ice-water, acidified with 2.5N hydrochloric acid and the collected solid triturated with a little ethyl ether. The crude 2-methyl-1-(p-methylthiobenzylidene)inden-3-acetic acid was collected.

Step C:

2-Methyl-1-(p-methylsulfinylbenzylidene)inden-3-acetic acid

To a solution of 2-methyl-1-(p-methylthiobenzylidene)inden-3-acetic acid (0.01 mole) in a mixture of methanol (250 ml.) and acetone (100 ml.) was added a solution of sodium periodate (3.8 g., 0.018 mole) in water (50 ml.) with stirring.

Water (450 ml.) was added after 18 hr. and the organic solvents removed under vacuum below 30° C.

The precipitated product, 2-methyl-1-(p-methylsulfinylbenzylindene)inden-3-acetic acid, was filtered, dried and recrystallized from ethyl acetate to give 3.0 g. 2-methyl-1-(p-methylsulfinylbenzylidene)inden-3-acetic acid.

Step D:
5-Fluoro-2-methyl-1-(p-methylsulfinylbenzylidene)inden-3-acetic acid

2-Methyl-1-(p-methylsulfinylbenzylidene)inden-3-acetic acid (2.25 g.) dissolved in 80 ml. of fluorotrichloromethane was ultraviolet irradiated and stirred at −15° C. for 80 min.; meanwhile 1.2 g. of fluoroxytrifluoromethane was passed in. The residue obtained after evaporation of the solvent was subjected to chromatography on a silica gel column, to give 5-fluoro-2-methyl-1-(p-methylsulfinylbenzylidene)inden-3-acetic acid, m.p. 188°–189° C.

EXAMPLE 16

Fluorination of Cyclohexane with Fluoroxytrifluoromethane

Cyclohexane (4.2 g.) was dissolved in 80 ml. of fluorotrichloromethane. The solution was cooled in a dry-ice-acetone bath and with vigorous stirring and irradiation with ultraviolet light, 2.7 g. of fluoroxytrifluoromethane was introduced over 45 minutes. After an additional 45 minutes under similar conditions the reaction mixture was washed with dilute sodium bicarbonate solution, dried over anhydrous magnesium sulfate, and the solvent was removed by distillation. Analysis of the residue by gas-liquid chromatography, gas-liquid chromatography-mass spectrometry and proton magnetic resonance spectroscopy showed fluorocyclohexane to be the major product.

EXAMPLE 17

Fluorination of Cyclohexane with Fluoroxyperfluoroethane

Cyclohexane (0.84 g., 0.01 mole) is dissolved in 50 ml. of fluorotrichloromethane, then while being ultraviolet irradiated and vigorously stirred, 1.5 g. of fluoroxypentafluoroethane is passed in during a period of 2 hours while the reaction mixture is cooled in a dry-ice-acetone bath. The solvent is evaporated by a stream of nitrogen gas and the residue distilled in vacuo at 210 mm Hg pressure to give fluorocyclohexane.

Employing the procedure of Example 16 or 17, but substituting for the cyclohexane employed therein, an equivalent amount of the cycloalkanes shown in Table II, there is produced the fluorocycloalkane products, also shown in Table II.

TABLE II

| Example | Starting Material | Product |
| --- | --- | --- |
| 18 | cyclopentane | fluorocyclopentane |
| 19 | cyclooctane | fluorocyclooctane |
| 20 | tetrahydronaphthalene | fluorotetrahydronaphthalene |
| 21 | decahydronaphthalene | fluorodecahydronaphthalene |
| 22 | cyclododecane | fluorocyclododecane |
| 23 | cycloheptane | fluorocycloheptane |
| 24 | chlorocyclohexane | fluorochlorocyclohexane |
| 25 | methylcyclohexane | fluoromethylcyclohexane |

EXAMPLE 26

Fluorination of 1-amino-adamantane with fluoroxytrifluoromethane

Into a solution of 1-amino-adamantane (1.51 g., 0.01 mole) in 40 ml. of liquid HF, 1.14 g. (0.011 mole) of fluoroxytrifluoromethane gas was introduced over a 30 min. period, under ultraviolet irradiation, while vigorously stirred and cooled in a dry-ice-acetone bath. After a further 30 min. of irradiation the solvent was blown off with a stream of nitrogen. The residue was dissolved in water, the pH was adjusted to pH 9 by addition of 1-N sodium hydroxide solution, the separated solid was extracted with diethyl ether (2 × 20 ml.), the combined extracts were dried overnight and evaporated to dryness, to give a colorless solid, which according to combined gas-liquid chromatography and mass spectrometric analysis consisted of, besides some unchanged starting material, a mixture of fluoro-1-amino-adamantanes. NMR spectroscopy indicated the latter compounds to be 3-fluoro-1-amino-adamantane and 4-fluoro-1-amino-adamantane. For preparative separation, the mixture was subjected to ion-exchange chromatography on Dowex 50-X-8 resin (a polystyrene nuclear sulfonic acid resin sold by Dow Chemical Co., Midland, Mich.) by elution with 4N hydrochloric acid.

EXAMPLE 27

2-Fluoroethylamine

Ethylamine (0.45 g., 0.01 mole) is dissolved in 35 ml. of liquid HF, then while irradiated by ultraviolet light and stirred under cooling in a dry-ice-acetone bath, 2.5 g. of fluoroxytrifluoromethane is passed into it over a period of 2½ hours. This is followed by 1½ hours more ultraviolet irradiation under similar conditions. The HF solvent is then distilled off and the residue analyzed by pmr and F nmr spectroscopy, to indicate that it represents about a 2:1 mixture of 2-fluoroethylamine and ethylamine, respectively (in the form of their hydrofluorides).

EXAMPLE 28

2,2-Difluoroethylamine

Employing the procedure substantially as described in Example 27, but by employing 5 g. of fluoroxytrifluoromethane instead of 2.5 g. and double the reaction time there is produced 2,2-difluoroethylamine.

EXAMPLE 29

2,2,2-Trifluoroethylamine

By employing the procedure substantially as described in Example 28 but introducing 9.5 g. of fluoroxytrifluoromethane over 6 hours, followed by 1½ hours of ultraviolet irradiation, 2,2,2-trifluoroethylamine is obtained as the main reaction product.

EXAMPLE 30

Fluorination of n-butylamine

Butylamine hydrochloride (1.1 g., 0.01 mole) was dissolved in 40 ml. of liquid HF, then under vigorous stirring at −78° C. and irradiation with ultraviolet light, 3.8 g. of fluoroxytrifluoromethane gas was passed into it, in 3 portions. First, 0.95 g. of fluoroxytrifluoromethane was added in 30 min., followed by an additional hour of ultraviolet irradiation; then with the same timing a second 0.95 g. portions of reagent, finally a 1.9 g.

portion of reagent was added. The HF solvent was removed by a nitrogen gas stream and the residue was analyzed by elementary analysis and pmr spectrum, to indicate the main product of the reaction to be 3,3-difluorobutylamine.2 HF.

EXAMPLE 31

5-Fluoro-L-isoleucine

L-Isoleucine (1.31 g., 0.01 mole) was dissolved in 40 ml. of liquid hydrogen fluoride. After cooling to, and while maintaining at −78° C., 1.04 g. of fluoroxytrifluoromethane was added over 30 minutes with vigorous agitation and irradiation with ultraviolet light. The solvent was evaporated at ambient temperature by passing nitrogen gas through the reaction mixture. As determined by proton magnetic resonance, and fluorine magnetic resonance, the major product was 5-fluoro-L-isoleucine.

The identity of the product was further proved by conversion to trans-3-methyl-L-proline by dissolving the product in 10 ml. of water, adjusting to pH 10 with 2.5 N sodium hydroxide solution, and allowing to stand overnight at ambient temperature. Analysis by Spinco-Beckman amino acid analysis indicated the presence of 0.503 g. of trans-3-methyl-L-proline (39% of theory).

EXAMPLE 32

3-Fluoro-D-alanine

Into a solution of 1.822 g. of D(−) alanine in 45 ml. of liquid HF, 0.6 g. of fluoroxytrifluoromethane gas was passed over a period of about 1 hour while being magnetically stirred, cooled in a dry-ice-acetone bath and irradiated by ultraviolet light. After 80 minutes further ultraviolet irradiation, 2 g. more of fluoroxytrifluoromethane gas was passed in while being ultraviolet irradiated over one and a half hours, followed by another 1 hour ultraviolet irradiation.

The solvent was removed by blowing through it a stream of nitrogen gas. The residue was dissolved in ice-water and a sample of it was analyzed in the Spinco-Beckman amino acid analyzer, indicating a 41% yield of 3-fluoro-D-alanine, and 32% of unreacted starting material. For isolation, the mixture was chromatographed on Dowex 50 × 8 cation exchange resin ($H^+$ form) (a polystyrene nuclear sulfonic acid resin sold by Dow Chemical Co., Midland, Michigan). For elution, 2N HCl was employed. From the appropriate fractions, by evaporation in vacuo, pure 3-fluoro-D-alanine hydrochloride was obtained. 3-Fluoro-D-alanine was liberated from the hydrochloride in water-pyridine-isopropanol mixture, m.p. 166°–168° C. (dec.); $[\alpha]_D$, −9.3° (1N-HCl).

EXAMPLE 33

3-Fluoro-L-Azetidine-2-carboxylic acid

Into a solution of 3.92 g. (0.039 mole) of L-azetidine-2-carboxylic acid in 60 ml. of liquid HF, 2.9 g. of fluoroxytrifluoromethane gas was introduced while being ultraviolet irradiated and stirred under cooling in a dry ice-acetone bath. The addition took about 75 min. The ultraviolet irradiation and stirring were continued for another 45 min., then 1.7 g. more of fluoroxytrifluoromethane was added in about 100 min., followed again by about 100 min. more of ultraviolet irradiation and stirring. Then 1.1 g. more of fluoroxytrifluoromethane was introduced over a 1 hour period, followed by about 30 min. additional ultraviolet irradiation. A fourth portion of reagent (2.2 g.) was introduced over a 1 hour period followed by 30 min. irradiation. Finally 1.5 g. of reagent was added in 30 min., followed by a similar period of ultraviolet irradiation. The solvent was then evaporated at room temperature. The residue was quenched in ice-water, evaporated in vacuo to dryness, re-dissolved in 50 ml. of water and chromatographed on about 1.4 l of Dowex 50 × 8 resin column (analyt. grade, 200–400 mesh). Eluants: 3 l of N/l aq. HCl discarded followed by 2.4 l of 2N aq. HCl (20 ml. fractions). Fractions No. 50–70 of the 2N HCl eluants contained the desired product. These were combined and evaporated to dryness in vacuo at room temperature. The residue was mixed with 1 ml. of water, 2 ml. of pyridine and 6 ml. of isopropanol to give 2.4 g. of colorless crystals of 3-fluoro-L-azetidine-2-carboxylic acid, m.p. 197° C. (dec.). Its assigned structure was confirmed by pmr spectroscopy and analysis, $C_4H_6NO_2F$, Calc.: C, 40.3; H, 5.1; N, 11.8; F, 16.00%; Found: C, 39.9; H, 5.0; N, 11.9; F, 16.2.

Employing the procedure substantially as described in Example 31, 32 or 33, but substituting for the amino acids used therein, an equivalent amount of the amino acid starting materials depicted in Table III, there are produced the fluorinated amino acids also described in Table III.

TABLE III

| Example | Starting Material | Product |
| --- | --- | --- |
| 34 | L-Proline | 3-fluoro and 4-fluoro-L-proline |
| 35 | D-glutamic acid | 3-fluoro and 4-fluoro-D-glutamic acid |
| 36 | L-aspartic acid | 3-fluoro-L-aspartic acid |
| 37 | Meso-2,6-diamino-pimelic acid | 4-fluoro-2,6-diaminopimelic acid |
| 38 | L-lysine | 4-fluoro-L-lysine |
| 39 | D-alanine (1) | 3,3-difluoro-D-alanine |
| 40 | D-alanine (2) | 3,3,3-trifluoro-D-alanine |
| 41 | Meso-2,6-diamino-imelic acid (1) | 4,4-difluoro-2,6-diamino-pimelic acid |

(1) by doubling the amount of reagent and reaction times
(2) by tripling the amount of reagent and reaction times

EXAMPLE 42

Fluoro-ε-aminocaprolactam

ε-Aminocaprolactam (2.26 g., 0.02 mole) is dissolved in 60 ml. of liquid HF. Fluoroxytrifluoromethane (10.4 g., 0.1 mole) is passed into the solution under ultraviolet irradiation over 5½ hours, while kept under vigorous stirring in a dry-ice-acetone cooling bath. After 1½ hours more ultraviolet irradiation under similar conditions, the solvent is removed by distillation. The residue is quenched with ice and water and extracted 3 times with ethyl acetate. The combined extracts are washed with aqueous sodium bicarbonate solution, dried over magnesium sulfate and evaporated to dryness, to give a mixture of C-fluorinated caprolactams, with the main components being difluorocaprolactam and trifluoro-caprolactam.

EXAMPLE 43

Fluoro-polydaprolactam 1.13 g. of Polycaprolactam (nylon-6; Zytel 2H Brand of DuPont) (0.01 unit g-mole) was dissolved in 40 ml. of liquid HF. Fluoroxytrifluoromethane (3.6 g.) was passed through the stirred solution over 1 hour, while it was being irradiated by ultraviolet light and cooled in a dry ice-acetone bath at about −78° C. After 15 min.

more ultraviolet irradiation, the cooling bath was removed and the solvent was evaporated (by a stream of nitrogen). To the residue, 15 ml. of methanol was added, then pyridine was added to neutrality (check by wet pH paper). The snow-white, solid precipitate, after drying in vacuo, weighed 0.95 g. and according to F analysis, it contained 17.3% fluorine (about 1.25 atom F per unit-mole).

In another experiment, Nylon-6 was subjected to similar fluorinating conditions, with the difference being that 9.5 g. of fluoroxytrifluoromethane was employed (passed in 2½ hours), followed by a further 40 min. of ultra-violet irradiation. By an isolation procedure similar to that described in Example 43, 1.5 g. of a snow-white polymer was obtained, containing 2.9 atoms of F per unit mole.

EXAMPLE 44

Fluorination of Acetic Acid

Acetic acid (1.2 g., 0.02 mole) is dissolved in 40 ml. of fluorotrichloromethane, then 3.5 g. of fluoroxytrifluoromethane is passed in during a 2 hour period under ultraviolet irradiation and stirring in a dry-iceacetone bath. After 1 hour more ultraviolet irradiation under similar conditions, the solvent is distilled off and residue is distilled through a micro fractionating column of the spinning band type, to give 1.1 g. of monofluoroacetic acid, b.p. 164°–165° C.

Under substantially similar conditions as described in Example 44, but employing 6.5 g. of fluoroxytrifluoromethane during a 3½ hour period, followed by another hour of ultraviolet irradiation, difluoroacetic is obtained as the main product.

Employing the procedure of Example 44, but with 10 g. of fluoroxytrifluoromethane passed in during 5 hours, a 3:1 mixture of trifluoroacetic acid and difluoroacetic acid is obtained.

EXAMPLE 45

Fluorination of Isobutyric acid

Into a solution of isobutyric acid (2.65 g., 0.03 mole) in 50 ml. of fluorotrichloromethane, 1.9 g. (0.0188 mole), of fluoroxytrifluoromethane gas was passed in ¾ hours, with stirring under ultraviolet light and while being cooled in dry-ice-acetone bath. After further, ultraviolet irradiation for another hour at −78° C., the solvent was removed by distillation and the residue was distilled at 2.5 mm Hg pressure. After a small forerun, 1.4 g. of colorless distillate was collected at 60°–85° C. According to nmr spectrum and elementary analysis, it was a mixture of some isobutyric acid, 2-fluoroisobutyric acid and 3-fluoroisobutyric acid.

Employing the procedure substantially as described in Examples 44 and 45, but substituting for the carboxylic acid used therein equivalent amounts of the carboxylic acids described in Table IV, there are produced the fluorinated carboxylic acids, also described in Table IV.

TABLE IV

| Example | Starting Material | Products |
| --- | --- | --- |
| 46 | Butyric acid | 3- and 4-fluorobutyric acid |
| 47 | Valeric acid | 4- and 5-fluorovaleric acid |
| 48 | Stearic acid (1) | Hexafluoro stearic acid |
| 49 | Lauric acid (1) | Tetrafluoro lauric acid |

(1) by increasing amount of reagent and reaction time

EXAMPLE 50

Fluorination of Chloroform

Into a solution of chloroform (1.20 g., 0.01 mole) dissolved in 35 ml. of dichlorodifluoromethane, fluoroxytrifluoromethane gas (3 g.) is passed in during a period of 4 hours, while being ultraviolet irradiated and stirred, under cooling in a dry ice-acetone bath. By preparative glc, 0.95 g. of fluorotrichloromethane (FREON 11) is isolated from the reaction product.

Employing the procedure of Example 50, but substituting for the chloroform used, therein, the haloalkanes described in Table V, there are produced the fluorinated haloalkanes also described in Table V.

TABLE V

| Example | Starting Material | Product |
| --- | --- | --- |
| 51 | Chloroethane | 1-chloro-2-fluoroethane |
| 52 | Chloroethane | 1-chloro-2,2-difluoroethane |
| 53 | 1-Chlorobutane | 4-fluoro-1-chlorobutane |
| 54 | 2-Chloropropane | 1-fluoro-2-chloropropane |
| 55 | 2-Chloropropane | 1,3-difluoro-2-chloropropane |
| 56 | 2-Chloro-2-methylpropane | 2-chloro-2-methyl-3-fluoropropane |

EXAMPLE 57

Fluorination of Polyethylene

Polyethylene powder was suspended in fluorotrichloromethane and exposed to ultraviolet light. Concurrently a slow stream of fluoroxytrifluoromethane gas was passed through under vigorous stirring, the reactor being immersed in a dry-ice acetone bath. After 2 hours of reaction time, the product was isolated by filtration, refluxed with methanol to remove traces of adhering hydrofluoric acid, and dried. Fluorine analysis indicated 3.1% F content in the product. The fluoropolyethylene thus obtained was characterized by substantially greater resistance against chemicals, as compared to the starting material, thus indicating the formation of a thin layer of fluorinated polymer on the surface of the particles.

EXAMPLE 58

Fluorination of Polystyrene

Polystyrene film (½ × 2 inch pieces) is exposed to fluoroxytrifluoromethane under ultraviolet irradiation at −78° C. After 1 hour reaction time, a polystyrene polymer with 2.45% F content is obtained. The material thus obtained exhibits greatly enhanced stability against chemicals, thus revealing the formation of a thin layer of fluorinated material on its surface.

EXAMPLE 59

Fluorination of Piperidine

Piperidine (4.25 g., 0.05 mole) was dissolved in 60 ml. of liquid hydrofluoric acid. Under stirring and irradiating at −78° C. with an x-ray source, fluoroxytrifluoromethane gas (7.5 g.) was passed in during 2½ hour period. After evaporation of the liquid hydrofluoric acid a mixture of piperidine .HF salt and fluoropiperidine .HF salt was obtained as a colorless solid.

EXAMPLE 60

4-(2-Phenyl-1,1,2,2-tetrafluoroethyl)-α,α-dimethylbenzylamine

4-Bromostilbene was reduced by standard procedure to 4-bromobibenzyl. In a nitrogen atmosphere 0.0205 g. atom of magnesium turnings were covered with 5 ml. of absolute ether; a crystal of iodine and a few ml. of a solution of 0.0183 mole of 4-bromobibenyl in 30 ml. of absolute ether were added. The Grinard reaction started after the mixture was heated to refluxing as the iodine color faded and the solution became cloudy. The remaining solution of the bromide was added rapidly dropwise and the mixture was stirred at reflux for 3 hr. During this period, a solution of 200 mg. of ethylene bromide in 0.5 ml. of ether was added in several portions in order to keep the magnesium clean. At the end of this period, almost all of the magnesium had reacted and a Gilman's test for Grignard reagent was strongly positive. The mixture was cooled in ice and a solution of 2.5 g. (0.04 mole) of acetone in 5 ml. of absolute ether was added rapidly dropwise. After stirring for 1 hr. at room temperature and 30 min. at reflux, the mixture was again cooled in ice and hydrolyzed by the dropwise addition of 2 ml. of water. The yellow ethereal solution was decanted from the gelatinous precipitate that then was re-extracted twice with ether. Evaporation of the combined washed and dried ethereal extracts under reduced pressure left the crude product as a viscous yellow oil. Purification was effected by chromatography on 210 g. of silica gel (Baker, 60–200 mesh powder for chromatography), eluting with chloroform. Evaporation of the solvent under reduced pressure gave 4-(2-phenethyl)-phenylpropanol-2.

Glacial acetic acid, 3.7 ml., was stirred, cooled in an ice-bath until it was about half frozen, and 0.7 g. (0.014 mole) of sodium cyanide was added in small portions, keeping the temperature at 15°–20° C. An ice-cold solution of 3.45 g. of concentrated sulfuric acid in 1.8 ml. of glacial acetic acid was added in portions, keeping the temperature at 20° C. by cooling in the ice-bath. The ice-bath then was removed and 0.0112 mole of 4-(2-phenethyl)phenylpropanol-2 was added in portions over 15 min. After stirring for 2 hr. at room temperature and 1 hr. at 30°–35° C., the mixture was allowed to stand overnight at room temperature. The mixture was poured into ice and water, neutralized with solid sodium carbonate, and the product was extracted into ether. Evaporation of the washed and dried ethereal extract under reduced pressure left a mixture of products as an off-white solid. Separation was effected by chromatography on 200 g. of silica gel (Baker) eluting with chloroform followed by methanol. Fractions eluted with methanol were combined and the solvent evaporated under reduced pressure to yield α,α-dimethyl-N-formyl-4-phenethylbenzylamine.

A solution of 0.0064 mole of α,α-dimethyl-N-formyl-4-phenethyl-benzylamine in 50 ml. of glacial acetic acid, 35 ml. of water, and 5 ml. of concentrated hydrochloric acid was heated to refluxing for 4 hr. Evaporation of solvents under reduced pressure left a pale brown solid residue that was dissolved in 35 ml. of absolute ethanol. The solution was decolorized with charcoal, filtered, and diluted with 200 ml. of absolute ether causing crystallization of 4-(2-phenethyl)-α,α-dimethylbenzylamine.HCl.

4-(2-Phenylethyl)-α,α-dimethylbenzylamine (6.70 g., 0.02 mole) and 50 ml. of anhydrous hydrogen fluoride are cooled to −78° C. to a dry ice-acetone bath. Then under stirring and ultraviolet irradiation, 1 g. of fluoroxytrifluoromethane is added over a period of 30 min. After 30 minutes more, an additional 1 g. of fluoroxytrifluoromethane is added as before. After a total of five such additions of reagent, the cold bath is removed and hydrogen fluoride and excess reagent is driven off with a stream of nitrogen gas. The residue is taken up in water and the fluorinated base is precipitated by addition of sodium hydroxide solution. The product is purified by ion exchange chromatography on Dowex 50-X-8 (H$^+$) by elution with 4N hydrochloric acid, to give 4-(2-phenyl-1,1,2,2-tetrafluoroethyl)-α,α-dimethylbenzylamine, m.p. 273°–274° C.

EXAMPLE 61

Fluorinated dimethyl polysiloxane

Dimethyl polysiloxane (2.25 g.) (Dow-Corning 200), is dissolved in 75 ml. of trichlorofluoromethane and photofluorinated at −78° C. by introduction of 4 g. of fluoroxytrifluoromethane over 5 hours with ultraviolet irradiation and vigorous stirring. After an additional 3 hours of irradiation and stirring the solvent is removed under a stream of nitrogen gas and finally vacuum. The residue consists of 3.3 g. of a viscous, clear, colorless liquid. Fluorine analysis shows 34% of organically bound fluorine.

EXAMPLE 62

Fluorinated Dimethyl Polysiloxane

Dimethyl polysiloxane (1.85 g. of Dow Corning 500) is dissolved in 45 ml. of trichlorofluoromethane and photofluorinated at −40° to −45° C. by introduction of 7 g. of fluoroxytrifluoromethane during a 6 hour period. The solvent is evaporated in vacuo to give a colorless oil with 41% fluorine content.

EXAMPLE 63

Fluorinated Methyl Propyl Polysiloxane

Methyl propyl polysiloxane (2.8 g.) is dissolved in 60 ml. of trichlorofluoromethane, 5 g. of finely powdered magnesium oxide is added and the mixture is photofluorinated at −78° C. by introduction of 8.5 g. of fluoroxytrifluoromethane over a 5 hour period while being irradiated with ultraviolet light. After 2 more hours the solvent is evaporated to give 3.2 g. of C-fluorinated methyl propyl polysiloxane with 21% fluorine content.

EXAMPLE 64

Fluorinated phenyl methyl polysiloxane

Phenyl methyl polysiloxane (1.1 g.) (Dow-Corning 550) is dissolved in 45 ml. of trichlorofluoromethane and treated with 3.5 g. of fluoroxytrifluoromethane over 5 hours, at −78° C. with ultraviolet irradiation and vigorous agitation. After 2 additional hours under the reaction conditions, the solvent is removed by distillation, finally under vacuum to leave a clear, colorless oil, having approximately 23% or organically bound fluorine.

EXAMPLE 65

Fluorinated dimethyl dichlorosilane

Dimethyl dichlorosilane (4.0 g.) is dissolved in 60 ml. of trichlorofluoromethane and photofluorinated by addition of 15 g. of fluoroxytrifluoromethane over 14 hours, at 78° C., with ultraviolet irradiation and vigorous stirring. After removal of the solvent, the residue is distilled, to give 7.2 g. of a mixture consisting of C-monofluorinated and C-polyfluorinated dimethyl dichloro silanes.

EXAMPLE 66

Fluorinated diphenyl-polysiloxane

Diphenyl polysiloxane (1.8 g.) is dissolved in 50 ml. of trichlorofluoromethane and fluorinated under irradiation with ultraviolet light by introduction of 6 g. of fluoroxytrifluoromethane over a period of 4 hours, while the temperature is maintained at about −78° C., and being vigorously stirred. After 3 hours of further U.V. irradiation under similar conditions, the solvent is distilled off (at the end in vacuo) to give a viscous clear liquid diphenyl-polysiloxane, containing 29% of organically bound fluorine.

What is claimed is:

1. A process for the substitutive fluorination of an organic compound containing at least one replaceable hydrogen atom, wherein the organic compound is either unsubstituted or substituted and is selected from the group consisting of
   1. mono- and polynuclear carbocyclic aromatic compounds,
   2. mono- and polynuclear alicyclic compounds,
   3. alkanes and alkenes,
   4. amino acids,
   5. fatty acids,
   6. polymers, and
   7. heterocycles which comprises contacting the organic compound in the liquid or solid state with a reagent selected from the group consisting of a fluoroxy perfluoroalkane of 1–5 carbon atoms and fluoroxy pentafluorosulfur in the presence of a free radical initiator which is light or ionizing radiation.

2. The process of claim 1, wherein the free radical initiator is light.

3. The process of claim 1, wherein the reagent is a fluoroxy perfluoroalkane of 1–5 carbon atoms.

4. The process of claim 1, wherein the reagent is fluoroxy pentafluorosulfur.

5. The process of claim 1, wherein the organic compound is in a solvent inert to fluorination.

6. The process of claim 1 in which the organic compound is 2-methyl-1-(p-methylsulfinylbenzylidene)iden-3-acetic acid.

7. The process of claim 1 in which the organic compound is 4-(2-phenylethyl)-$\alpha,\alpha$-dimethylbenzylamine.

8. The process of claim 1 in which the organic compound is polycaprolactam, polyethylene, or polystyrene.

* * * * *